United States Patent
Buschnakowski et al.

(10) Patent No.: US 8,753,495 B2
(45) Date of Patent: Jun. 17, 2014

(54) ELECTROCHEMICAL HALF CELL, ELECTROCHEMICAL SENSOR AND METHOD FOR MEASURING AT LEAST ONE MEASURED VARIABLE OF A MEASURED MEDIUM WITH AN ELECTROCHEMICAL SENSOR

(75) Inventors: Stephan Buschnakowski, Chemnitz (DE); Lothar Auerswald, Dobeln (DE); Thomas Wilhelm, Halle (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 43 days.

(21) Appl. No.: 13/338,818

(22) Filed: Dec. 28, 2011

(65) Prior Publication Data
US 2012/0168321 A1     Jul. 5, 2012

(30) Foreign Application Priority Data

Dec. 29, 2010   (DE) .......................... 10 2010 064 312
Nov. 17, 2011   (DE) .......................... 10 2011 086 591

(51) Int. Cl.
*G01N 27/26*   (2006.01)

(52) U.S. Cl.
USPC ........ 204/433; 204/435; 205/787.5; 205/789; 324/438

(58) Field of Classification Search
USPC ................. 204/409, 411, 416–420, 433, 435; 324/439; 205/787.5, 789
See application file for complete search history.

(56) References Cited

U.S. PATENT DOCUMENTS

| | | | |
|---|---|---|---|
| 5,830,338 A * | 11/1998 | Seto et al. ...................... 204/416 |
| 2001/0045357 A1* | 11/2001 | Broadley et al. .............. 204/435 |
| 2003/0152469 A1* | 8/2003 | Dante et al. ................ 417/413.2 |
| 2011/0061526 A1* | 3/2011 | Wackerle et al. ................. 92/96 |
| 2011/0308947 A1 | 12/2011 | Wilke |

FOREIGN PATENT DOCUMENTS

| | | |
|---|---|---|
| CH | 680311 A5 | 7/1992 |
| DE | 10 2008 056 899 A1 | 2/2010 |
| DE | 102008056899 A1 | 2/2010 |
| DE | 10 2008 055 082 A1 | 7/2010 |
| DE | 102008055082 A1 | 7/2010 |
| DE | 102009055092 A1 | 6/2011 |
| EP | 1 544 608 A1 | 6/2005 |
| EP | 1544608 A1 | 6/2005 |
| WO | WO2009052842 * | 4/2009 |

OTHER PUBLICATIONS

German Search Report in corresponding German Application No. 10 2011 086 591.8, dated Sep. 6, 2012.
German Search Report.
German Language Search Report dated Oct. 17, 2011.

* cited by examiner

*Primary Examiner* — Bach Dinh
(74) *Attorney, Agent, or Firm* — Bacon & Thomas, PLLC

(57) ABSTRACT

An electrochemical half cell for application in an electrochemical sensor, wherein a fill electrolyte of the half cell is in contact with an external medium via a liquid junction, characterized in that the liquid junction is controllable as regards its permeability and/or its flow.

23 Claims, 1 Drawing Sheet

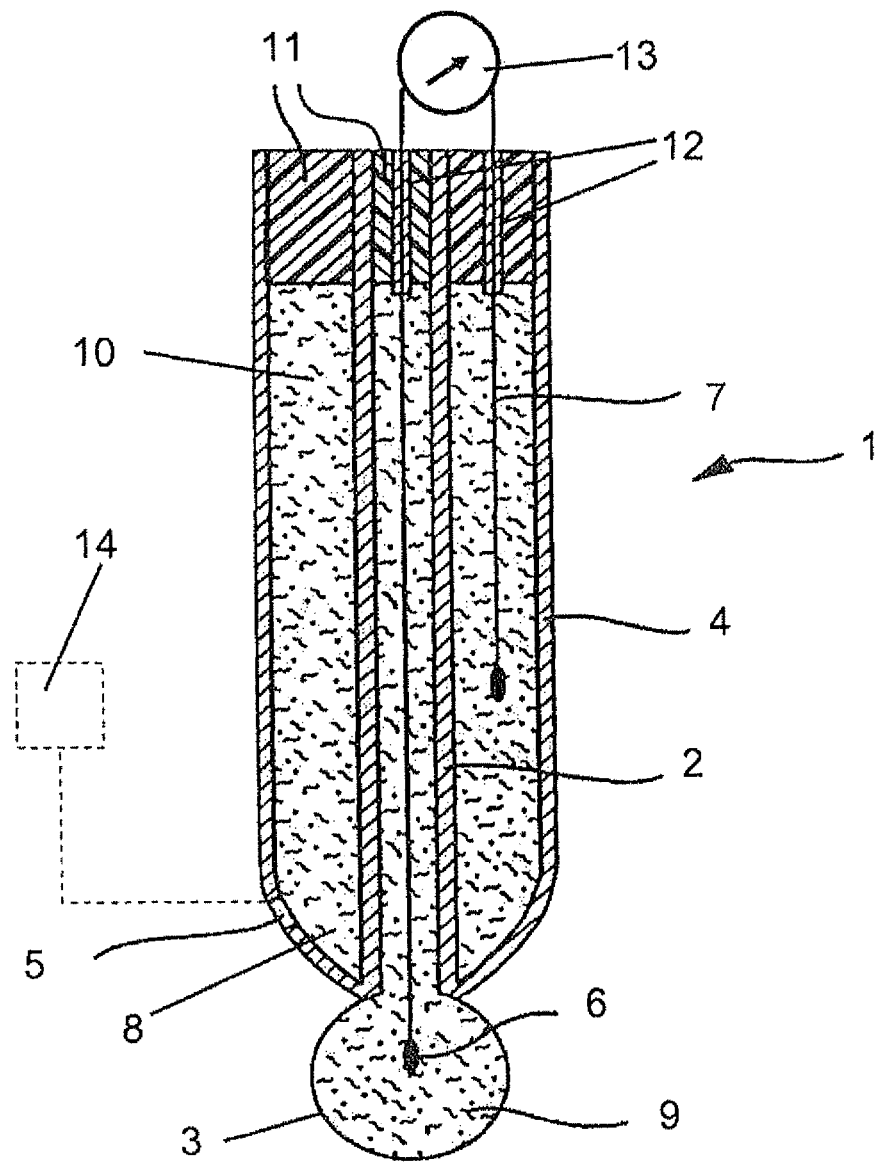

ELECTROCHEMICAL HALF CELL, ELECTROCHEMICAL SENSOR AND METHOD FOR MEASURING AT LEAST ONE MEASURED VARIABLE OF A MEASURED MEDIUM WITH AN ELECTROCHEMICAL SENSOR

TECHNICAL FIELD

The invention relates to: an electrochemical half cell for application in an electrochemical sensor, wherein a fill electrolyte of the half cell is in contact with an external medium via a liquid junction; an electrochemical sensor; and a method for measuring at least one measured variable of a measured medium with the electrochemical sensor.

BACKGROUND DISCUSSION

Electrochemical sensors can be, for example, potentiometric or amperometric sensors. An established embodiment of an electrochemical sensor of the field of the invention is, for example, a potentiometric, single-rod, measuring chain for the electrochemical measuring of pH values in many fields of chemistry, environmental analytics, medicine, industry and water management. Such an electrochemical sensor unites a measuring electrode and a reference electrode in one assembly. Utilized as reference electrode is, as a rule, a silver/silver-chloride electrode, which forms a constant potential. This silver/silver-chloride electrode is immersed in a reference electrolyte, for example, KCl-solution, which is located in an annular space around the measuring electrode. Depending on the embodiment, the annular space can contain, besides the reference electrolyte, also one or more bridge electrolytes. The electrolyte, which is in contact with the measured medium at the liquid junction, is referred to in the following as the fill electrolyte. The measuring electrode includes, usually, a glass tube, which is closed facing the medium to be measured with a glass membrane and which is filled with a buffer solution of known pH-value and known chloride ion activity. For sensing the pH dependent potential, likewise a silver/silver chloride wire is immersed in the buffer solution. The Ag/AgCl-electrode forms with the buffer solution a first galvanic half cell, which is in contact with the measured medium via the glass membrane, at which a pH-dependent potential forms.

An amperometric sensor can comprise, for example, a three-electrode circuit with a working electrode, a counterelectrode and a non electrical current bearing, reference electrode. The reference electrode, through which electrical current does not flow, here and in the following likewise referred to as a half cell, can be embodied in an equal manner as the previously described Ag/AgCl-reference half-cell.

The glass tube with the measuring electrode is surrounded by an annular space containing the reference electrode. In a pH-sensor, e.g. a pH, single-rod, measuring chain, usually a silver/silver chloride, reference electrode is used, in order to obtain a reference potential. This Ag/AgCl-electrode forms with the reference electrolyte with known chloride ion activity a second galvanic half cell, which is in contact with the measured medium via an ionically conducting contact, a so-called liquid junction or diaphragm. The liquid junction is placed in the glass wall of the glass container and is composed, for example, of a porous ceramic material, at which charge exchange can occur. This charge exchange is referred to as electrolytic contact.

Due to the character of the liquid junction, measured medium can penetrate into the annular space, and fill electrolyte contained in the annular space can escape from the glass container into the measured medium. This can lead to bleeding or poisoning of the reference electrode, or to the forming of disturbing, diffusion- and streaming potentials through impurities or plugging at the liquid junction, which corrupt the pH-measuring. The bleeding can lead to depletion of the potential determining species in the reference half-cell. A further problem caused by the character of the liquid junction can be that the sensor dries during a long, dry storage. There are therefore special requirements for the storage of such sensors; for example, it must be assured that the liquid junction is immersed during storage in a liquid, for example, a KCl-solution.

SUMMARY OF THE INVENTION

An object of the invention, thus, is to provide an electrochemical half cell and an electrochemical sensor, which reliably prevent the forming of disturbing diffusion- and streaming potentials at the liquid junction and which have increased long time stability and/or permit dry storage.

According to the invention, the object is achieved by the feature that the liquid junction is controllable as regards its permeability and/or its flow. This has the advantage that, through the application of a controllable liquid junction, the ion exchange between the measured medium and the fill electrolytes can be actively controlled. Moreover, the drift behavior of the reference electrode is improved, since depletion of the potential determining species and the forming of disturbing potentials at the liquid junction, which superimpose on the measurement potential, are suppressed. Thus, a correct reference potential is reliably output.

Advantageously, the permeability and/or the flow of the liquid junction are/is increasable during a measurement. Through the improved contact of the measured medium with the fill electrolyte during the measurement, a correct reference voltage signal is assured from the reference electrode. Upon termination of the measurement, the liquid junction can, at any time, be reclosed, in order, thus, to suppress exchange of liquids, such as escape of fill electrolyte from the annular space into the measured medium and also the entry of measured medium into the annular space. The permeability of the liquid junction is increased just for the point in time of the measuring of the measured variable of the measured medium, so that contamination of the liquid junction and, consequently, resulting corruption of the reference signal are suppressed.

In a variant, the permeability and/or the flow are/is controllable via the internal pressure of a reference half-cell. In this way, additional control elements can be omitted.

In an embodiment, the liquid junction is closable. The liquid junction is only opened during the measurement with the electrochemical half cell, in order, at this point in time, to assure ion exchange between measured medium and fill electrolyte for setting the reference potential.

Especially, the liquid junction includes a check valve. In this way, a flowing out of the fill electrolyte located in the half cell into the measured medium is reliably suppressed.

In a variant, the liquid junction includes a piezo nozzle, whose passageway is controllable during measurement. In such case, the connection between the measured medium and the fill electrolyte can be especially simply controlled, since the material of the piezo nozzle deforms under the influence of an electrical voltage. The piezo nozzle is so embodied, in such case, that its aperture changes under the influence of the voltage. The piezo nozzle can, in such case, be advantageously placed perpendicularly, horizontally or overhanging in the glass wall, in order, supplementally, to prevent plugging and contamination.

The liquid junction can be embodied as a "normally closed" variant, wherein the liquid junction is only opened when a measuring is to be performed. In the previously described variant, in which the liquid junction includes a piezo nozzle, this can be so embodied that the liquid junction is closed in the voltageless state and is opened upon applying a voltage for deforming the piezo nozzle. If the electrochemical half cell, or the electrochemical sensor, is to be stored dry for a long time, or used in measurement operation only rarely for performing isolated measurements, so that the liquid junction remains closed over a large part of the time, this embodiment is quite advantageous.

In another embodiment the liquid junction can be embodied as "normally open", wherein the liquid junction can be closed during storage or over a longer period of time, in which no measurements are to be performed. In the variant, in which the liquid junction includes a piezo nozzle, this can be so embodied that, in the voltageless state, the piezo nozzle of the liquid junction is opened and, upon applying a voltage for deforming the piezo nozzle, the nozzle is further, or completely, closed.

In addition to actively controlling elements, such as the piezo nozzle, the liquid junction can also include porous elements, such as ceramic- or Teflon diaphragms.

Especially, a potential forming system in the electrochemical half cell is an electrode of $2^{nd}$ kind, especially a silver-silver halogenide electrode.

A further development of the invention relates to an electrochemical sensor for measuring at least one measured variable of a measured medium, which includes at least one electrochemical half cell and at least one other sensitive surface and/or an electrochemical half cell, wherein the at least one electrochemical half cell has a liquid junction, which is controllable as regards its permeability and/or its flow. This has the advantage that, through the application of a controllable liquid junction, ion exchange between the measured medium and the fill electrolyte can be actively controlled. Moreover, the drift behavior of the reference electrode is improved, since, due to suppressing disturbing potentials at the liquid junction, which oppose the measurement potential and/or due to slower depletion of the reference half-cell in potential determining species, a correct reference potential is reliably output.

In an embodiment, at least one measured variable of the measured medium is an activity, especially a proton activity, a pH-value or a redox-potential. The electrochemical sensor is, thus, very adaptable for different measurement purposes.

In an especially cost effective and simple form of embodiment, at least one half cell is in contact with an external medium via a glass membrane. In other embodiments, the sensor includes at least one sensitive region, for instance, in the form of a gate of an ion-selective field effect transistor or the surface of a metal-metal oxide electrode. The sensitive region can furthermore be the surface of a layered stack of an EIS-sensor (EIS=electrolyte-insulator-semiconductor structure), a metal electrode of a redox sensor or a non-metallic, redox electrode.

The half cell can also be a component of an amperometric sensor, for example, a no electrical current bearing, reference electrode of an amperometrically operated, three-electrode circuit with working-, counter- and reference electrodes.

Advantageously, the piezo nozzle is connectable with a voltage control, which activates the piezo nozzle as a function of the measuring procedure by applying a voltage for increasing or reducing the diameter of the piezo nozzle. Such a voltage control unit is known per se and can be simply inserted into the structural unit of the electrochemical sensor.

In an additional variant, the piezo nozzle of the voltage control unit receives a voltage control pattern, which is clocked and/or variable as a function of the measuring procedure. Thus, the opening of the piezo nozzle can be automatically obtained, when a measuring procedure is desired.

Alternatively, the piezo nozzle of the voltage control unit receives a voltage control pattern, which is embodied rectangularly shaped as a function of the measuring procedure. This embodiment is especially advantageous, when a measuring procedure is to be executed at regular intervals, so that, as a function of which value the voltage assumes, the piezo nozzle is opened or closed.

Another further development of the invention relates to a method for measuring at least one measured variable of a measured medium with an electrochemical sensor, which has a liquid junction, whose permeability and/or flow are/is modulated during the measurement. This has the advantage that ion exchange between the measured medium and the fill electrolyte is implemented only in the actual instant of measurement. This has the result that contamination of the electrochemical sensor is suppressed, whereby the lifetime of the electrochemical sensor is lengthened. The opening of the liquid junction only during the measurement improves the drift behavior of the electrochemical sensor and prevents escape of fill electrolyte into the measured medium and depletion of the reference electrolyte at points in time outside of the measurement, as well as preventing entering of measured liquid into the fill electrolyte.

Advantageously, the modulation of the permeability and/or the flow of the liquid junction is achieved by the electrical activating of a piezo nozzle. In this way, it is assured that the connection between the measured medium and the fill electrolyte can be actively controlled. The piezo nozzle can even be completely closed, when no measuring procedure is occurring. In this way, contamination and plugging of the piezo nozzle is prevented and residence of the half cell in a dry environment enabled.

Alternatively, the internal pressure of the reference half-cell is controllable.

BRIEF DESCRIPTION OF THE DRAWING FIGURE

The invention permits numerous forms of embodiment. One thereof will now be explained in greater detail based on the drawing, the sole FIGURE of which shows as follows:

FIG. 1 is a longitudinal section through a pH-sensor in the form of a single-rod, measuring chain.

FIG. 1 shows a pH-sensor 1, which is embodied as a single-rod, measuring chain. The single-rod, measuring chain 1 includes an inner tube 2 with a pH-membrane 3 and an external glass tube 4, which surrounds, and is connected with, the inner tube 2. Additionally, a piezo nozzle 5, which serves as liquid junction, is placed in the outer glass tube 4. For sensing measuring- and, respectively, reference potentials, silver/silver chloride electrodes 6, 7 are arranged, respectively, in the inner tube 2 and in the annular space 8 between the inner tube 2 and the outer glass tube 4. In such case, the silver/silver chloride electrode 6 used as measuring electrode is led within the inner tube 2 for sensing a measurement potential, while the silver/silver chloride electrode 7 used as reference electrode is arranged in the annular space 8 between inner tube 2 and outer glass tube 4 for bringing off a reference potential.

The inner tube 2 is filled with a buffer solution 9, which covers also the glass membrane 3. The annular space 8 is filled with a fill electrolyte 10, for example, potassium chloride solution (KCl), and is in contact with the liquid junction embodied, for example, as a piezo nozzle 5. After filling the inner tube 2 with the buffer solution 9 and, respectively, the annular space 8 with the fill electrolyte 10, the inner tube 2 and the annular space 8 must be sealed in suitable manner with plug, or stopper, means 11, wherein, supplementally, feedthroughs 12 for the electrode wires of the measuring electrode 6 and the reference electrode 7 are provided. The measuring electrode 6 and reference electrode 7 led out from the pH-sensor 1 are connected with a measurement transmitter 13, which outputs the pH-value, which i is measured n the case of immersion of the pH-sensor 1 into a measured medium. Moreover, the piezo nozzle 5 is electrically connected with a voltage supply 14, which is shown schematically in FIG. 1.

If, now, the pH-value of a measured medium is to be determined, the pH-sensor 1 with its pH-membrane 3 and the liquid junction 5 as measuring head are immersed into the measured medium. In such case, the pH-sensor 1 forms with the measured medium a galvanic cell. The cell voltage of the galvanic cell depends on the hydrogen-ion concentration of the measured medium. The pH-membrane 3 represents, in such case, the part of the pH-sensor 1 sensitive for the hydrogen ions. The Ag/AgCl-electrode 6 forms with the buffer solution 9 a first galvanic half element, or half cell, which is in contact with the measured solution via the glass membrane 3, while the Ag/AgCl-electrode 7 with the fill electrolyte 10 in the outer glass tube 4 forms a second galvanic half element, or half cell, which is in contact with the measured solution via the liquid junction 5. The inner potential is registered on the electrode terminal of the measuring electrode 6 of silver/silver chloride, while the outer potential is registered via the electrode terminal of the reference electrode 7.

The liquid junction in the form of the piezo nozzle 5 has, in such case, the purpose of establishing a charge exchange (electrolytic contact) between the fill electrolyte 10 and the measured medium. In such case, the piezo nozzle 5 is operated by the voltage supply 14 only at the point in time, when a measuring is desired. At other points in time, in which no measuring is being performed with the pH-sensor 1, the pH-sensor 1 remains, in spite of this, immersed in the measured medium. The piezo nozzle 5 is closed, so that no ion exchange can occur between the measured medium and the fill electrolyte 10.

In order to match the open times of the piezo nozzle 5 to the measuring rhythm of the pH-sensor 1, the voltage, which is provided the piezo nozzle 5 by the voltage supply 14, is output clocked. In this way, the opening- and closing events of the piezo nozzle 5 can be automatically set. The application of the piezo nozzle 5 makes use of the inverse piezo effect, in the case of which materials, upon the applying of an electrical voltage, change their shape. By applying the electrical voltage, the piezo nozzle 5 blocks the connection between the measured medium and the fill electrolyte 10 in the annular space 8.

Furthermore, it is thereby reliably prevented that contamination and pluggings deposit at the piezo nozzle 5. This prevents the formation of measurement disturbing diffusion- and streaming potentials. The fill electrolyte 10 is, in such case, not contaminated and does not deplete, which significantly lengthens the lifetime of the pH-sensor 1.

The invention claimed is:

1. An electrochemical half-cell for application in an electro-chemical sensor, wherein:

a fill electrolyte of the half cell is in contact with an external medium via a liquid junction, and the liquid junction is controllable with regard to its permeability and/or its flow;

said liquid junction is closable;

said liquid junction is embodied as normally closed; and the liquid junction comprises a piezo nozzle, which controls a connection between the external medium and the fill electrolyte during the measurement in a measured medium.

2. The electrochemical half cell as claimed in claim 1, wherein:

the permeability and/or the flow of the liquid junction are/is increasable during a measurement.

3. The electrochemical half cell as claimed in claim 1, wherein:

the permeability and/or the flow are/is controllable via internal pressure of the half cell.

4. The electrochemical half cell as claimed in claim 1, wherein:

the liquid junction comprises a check valve.

5. The electrochemical half cell as claimed in claim 1, wherein:

the piezo nozzle is embodied in such a manner that it is closed in a voltageless state and is opened by applying an electrical voltage.

6. The electrochemical half cell as claimed in claim 1, wherein:

a potential forming system is a silver-silver halogenide electrode.

7. The electrochemical half cell as claimed in claim 1, wherein:

the liquid junction is only opened when a measurement is to be performed.

8. An electrochemical sensor for measuring at least one measured variable of a measured medium, wherein:

the sensor comprises at least one electrochemical half cell for application in an electro-chemical sensor;

a fill electrolyte of the half cell is in contact with an external medium via a liquid junction, and the liquid junction is controllable with regard to its permeability and/or its flow;

said liquid junction is closable;

said liquid junction is embodied as normally closed;

the liquid junction comprises a piezo nozzle, which controls a connection between the measured medium and the fill electrolyte during measurement;

the piezo nozzle connected with a voltage control unit, which activates the piezo nozzle with a voltage to change the connection between measured medium and fill electrolyte as a function of a measuring procedure; and at least one other sensitive surface and/or at least one other electrochemical half cell.

9. The electrochemical sensor as claimed in claim 8, wherein:

at least one measured variable of the measured medium is a capacitance, an impedance or an activity, especially a proton activity, a pH-value or a redox-potential.

10. The electrochemical sensor as claimed in claim 8, wherein:

the at least one other half cell is in contact with the measured medium, via an ion-selective glass membrane.

11. The electrochemical sensor as claimed in claim 8, wherein:

the sensor comprises at least one sensitive surface, which is a gate of an ion-selective, field effect transistor, a surface of an EIS-sensor layered stack, a metal electrode of a redox sensor, a non-metallic redox electrode or a surface of a metal-metal oxide electrode.

12. The electrochemical sensor as claimed in claim 8, wherein:
the piezo nozzle receives from the voltage control unit a voltage control pattern, which is clocked and/or variable as a function of the measuring procedure.

13. The electrochemical sensor as claimed in claim 8, wherein:
the liquid junction is only opened when a measurement is to be performed.

14. A method for measuring at least one measured variable of a measured medium with an electrochemical sensor for measuring said measured variable, wherein:
the sensor comprises at least one first electrochemical half cell for application in an electro-chemical sensor, wherein a fill electrolyte of the half cell is in contact with an external medium via a liquid junction, and the liquid junction is controllable with regard to its permeability and/or its flow;
said liquid junction is closable;
said liquid junction is embodied as normally closed; and
at least one other sensitive surface and/or at least one second electrochemical half cell, the method comprising the step of:
the permeability and/or the flow of the liquid junction are/is modulated during measurement.

15. The method as claimed in claim 14, wherein:
the modulation of the permeability and/or the flow of the liquid junction is achieved by electrical activating of a piezo nozzle.

16. The method as claimed in claim 15, comprising:
opening the piezo nozzle, when a measuring procedure is desired by applying a voltage control pattern to the piezo nozzle, said voltage control pattern being clocked and/or variable as a function of the measuring procedure.

17. The method as claimed in claim 14, wherein:
the internal pressure of the reference half-cell is controllable.

18. The method as claimed in claim 14, wherein:
the liquid junction is only opened when a measurement is to be performed.

19. An electrochemical sensor for measuring at least one measured variable of a measured medium, wherein:
the sensor comprises at least one first electrochemical half cell for application in an electro-chemical sensor;
a fill electrolyte of the half cell is in contact with an external medium via a liquid junction, and the liquid junction is controllable with regard to its permeability and/or its flow;
at least one sensitive surface and/or at least one second electrochemical half cell;
said liquid junction comprises a piezo nozzle, which controls a connection between the measured medium and the fill electrolyte during measurement; and
the piezo nozzle is connected to a voltage control unit, which is embodied to activate the piezo nozzle as a function of a measuring procedure by applying a voltage for increasing or reducing the diameter of the piezo nozzle.

20. The electrochemical sensor as claimed in claim 19, wherein:
said piezo nozzle receives from the voltage control unit a voltage control pattern, which is clocked and/or variable as a function of the measuring procedure.

21. The electrochemical sensor as claimed in claim 19, wherein:
said control unit receives a voltage control pattern, which is clocked as a function of the measuring procedure, so that the piezo nozzle is opened, when a measuring procedure is desired.

22. The electrochemical sensor as claimed in claim 19, wherein:
the at least one other half cell is in contact with the measured medium, via an ion-selective glass membrane.

23. The electrochemical sensor as claimed in claim 19, wherein:
the sensor comprises at least one sensitive surface, which is a gate of an ion-selective, field effect transistor, a surface of an EIS-sensor layered stack, a metal electrode of a redox sensor, a non-metallic redox electrode or a surface of a metal-metal oxide electrode.

* * * * *